United States Patent [19]

Middlebrook et al.

[11] 4,296,254

[45] Oct. 20, 1981

[54] TRANSETHERIFICATION IN AMIDES

[75] Inventors: Robert E. Middlebrook, Coral Gables; George R. Harvey, Miami, both of Fla.; John P. Chupp, Kirkwood, Mo.

[73] Assignee: Monsanto Company, St. Louis, Mo.

[21] Appl. No.: 133,752

[22] Filed: Mar. 25, 1980

[51] Int. Cl.³ .............................................. C07C 102/00
[52] U.S. Cl. ................................ 564/214; 260/340.7; 260/347.3; 260/464; 260/465 D; 564/210; 564/211; 560/20; 560/43; 560/125
[58] Field of Search ......... 260/561 HL, 562 B, 347.3, 260/340.7, 465 D, 464; 464/210, 211, 214; 560/20, 43, 125

[56] References Cited

U.S. PATENT DOCUMENTS

| | | | |
|---|---|---|---|
| 2,617,747 | 11/1952 | Rasmussen et al. | 260/561 |
| 2,914,553 | 11/1959 | Gasson et al. | 560/89 |
| 3,692,691 | 9/1972 | Meltsner | 252/404 |
| 4,156,784 | 5/1979 | Dockner et al. | 560/157 |

OTHER PUBLICATIONS

Petrov et al. Chem. Abstracts 56, (1961), 3511i.
Wagner et al. Synthetic Organic Chemistry, John Wiley & Sons, N.Y., N.Y.; 1955, p. 647.

*Primary Examiner*—Arthur P. Demers
*Attorney, Agent, or Firm*—William I. Andress; Donald W. Peterson

[57] ABSTRACT

The disclosure herein pertains to the preparation of N-(alkoxymethyl)- and other N-methylene ether-substituted 2-haloacetamides from other N-methylene ether-substituted 2-haloacetamides and the appropriate alcohol by a transetherification process.

19 Claims, No Drawings

TRANSETHERIFICATION IN AMIDES

BACKGROUND OF THE INVENTION

The invention herein pertains to the field of processes for the preparation of 2-haloacetamides.

DESCRIPTION OF THE PRIOR ART

The preparation of various ether compounds by transetherification with other ethers or alcohols is known. Illustrative of the prior art in this field might be cited the alcoholysis of β-alkoxymethyl ethers to obtain glycerol U.S. Pat. No. 2,211,626); the reaction of cyclic formals of tertiary glycols with lower aliphatic alcohols to give tertiary glycol monoalkyl ethers (U.S. Pat. No. 2,426,015); the reaction of alcohols with vinyl or allyl ethers (U.S. Pat. Nos. 2,566,415, 2,760,990 and 3,250,814); the reaction of one ether with another ether (U.S. Pat. No. 2,746,995) and the transetherification of polyhydric alcohols with a diallyl ether of a polyhydric alcohol. The process described in the foregoing exemplary references use a variety of reaction conditions of times, temperatures, acidic or basic catalysts and co-catalysts. However, the prior art has not been found to disclose the transetherification of 2-haloacetamides with alcohols as described herein.

The present invention as exemplified in working embodiments below provides an expedient alternative to more complicated processes for producing 2-haloacetamides substituted on the nitrogen atom with an alkoxymethyl or other N-methylene ether groups which are very beneficial herbicidal compounds. For example, prior art processes for producing these herbicides involved the reaction of the appropriately-substituted aniline with formaldehyde to produce the corresponding precursor substituted-phenylazomethine which was then reacted with a haloacetylating agent to produce the intermediate N-(haloalkyl) starting material which was then reacted with an alcohol to produce the final product.

SUMMARY OF THE INVENTION

This invention relates to a transetherification process to produce N-(alkoxymethyl)- and other N-methylene ether-substituted 2-haloacetamides by reacting the necessary alcohol with a different N-(alkoxymethyl)- or N-methylene ether-substituted-2-haloacetamide. The process is conducted in a solvent (preferably the reactant alcohol itself) at elevated temperatures, typically reflux, in the presence of an acid catalyst; optionally, a molecular sieve may be used to remove by-product alcohol and water.

In more particular, the present invention relates to a process for the preparation of N-methylene ether-substituted-2-haloacetamides having the formula

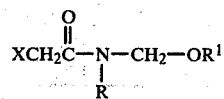   I which comprises transetherification of N-methylene ether-2-haloacetamides of the formula

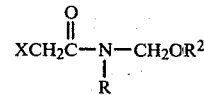   II with a compound of the formula $$R^1OH \qquad \text{III}$$

where in the above formulae
X is chloro, bromo or iodo,
R is a phenyl or cycloalkenyl radical or a phenyl or cycloalkenyl radical substituted with lower alkyl, alkoxy, polyalkoxy or alkoxyalkyl having up to 6 carbon atoms, halogen, $NO_2$, $-CF_3$ or an O- or S-containing heterocyclylmethoxyloxy radical containing up to 6 carbon atoms and
$R^1$ and $R^2$ are different $C_{1-6}$ alkyl, haloalkyl, alkenyl, haloalkenyl, alkynyl, haloalkynyl, alkoxyalkyl, cycloalkyl, cyanoalkyl or lower alkoxycarboalkyl radicals or 1,3-dioxolanylmethyl which may be substituted with lower alkyl groups.

The transetherification process herein is conducted in an inert solvent (preferably the compound of Formula III) at temperatures within the range of 0°–200° C., preferably room-temperature to 150° C.; in the presence of an acid catalyst and, optionally a molecular sieve, e.g., Type 3A. A particular advantage of the use of a molecular sieve is that it selectively absorbs both alcohol and water by-products in the presence of higher boiling alcohols; these by-products may also be removed by conventional distillation.

In preferred embodiments R is a 1-cycloalken-1-yl radical substituted with one or more lower alkyl groups preferably in the 2 or 6 position, or a phenyl radical also preferably substituted in at least one o-position with a lower alkyl, alkoxy, alkoxymethyl, halogen or $-CF_3$ radical; in either case the substituents, if more than one, may be the same or different.

In one preferred embodiment, the present process is suited to the transetherification of 2',6'-diethyl-N(methoxymethyl)-2-chloroacetanilide (common name alachlor) with n-butanol to produce the higher N-alkoxymethyl homolog 2',6'-diethyl-N-(n-butoxymethyl)-2-chloroacetanilide (common name butachlor), a leading rice herbicide; or vice-versa, i.e., the transetherification of butachlor with methanol to produce alachlor.

As used herein the term "lower alkyl" means an alkyl group having from 1–6 carbon atoms.

The unique and unobvious character of the present invention is made manifest by reference to expected reactions which do not occur when N-(alkoxymethyl)-2-haloacetamides are transetherified by alcohols according to this invention. For example, in starting N-alkoxymethyl-2-haloacetamides having alkoxy or alkoxyalkyl radicals substituted on the anilide ring, there are two ether linkages which could interchange with the reactant alcohol. However, according to the process of this invention, only the ether linkage in the N-methylene ether moiety is interchanged, leaving the anilide-substituted ether linkage intact.

Furthermore, the N-alkoxymethyl-2-halo-acetamide starting materials used herein are amide aminals, although for convenience they may be and are referred to as N-methylene ether-substituted 2-haloacetamides. Accordingly, it is not at all obvious or expected that traansetherification would occur at all, since equally feasible and expected reactions could occur, e.g., cleavage could occur at the bond between the alkoxymethyl radical and the amide nitrogen atom resulting in the formation of an N-hydrogen-2-haloacetamide and a dialkyl formal (R'OCH$_2$OR) byproduct; but such reaction does not occur in the process of the present invention.

DETAILED DESCRIPTION OF THE INVENTION

EXAMPLE 1

Alpha-chloro-N-(2,6-dimethylcyclohexen-1-yl)-N-(methoxymethyl) acetamide (6.1 g, 0.025 mol), isobutanol (150 ml) and three drops of methane sulfonic acid were refluxed in a 250 ml flask through a soxhlet extractor filled with 22 g of activated 3A molecular sieve in a thimble. Refluxed for two hours. Volatiles removed in vacuo, leaving an oil which was washed with 100 ml of 5% Na$_2$CO$_3$ aqueous, and extracted with ether. Ether layer was dried over MgSO$_4$, filtered and evaporated leaving an oil which was vacuum distilled (120° C. at 0.1 mm) to give 4.0 g (67% yield) of clear colorless oil.

Anal. for C$_{15}$H$_{26}$ClNO$_2$ (%):

| Element | Calc'd | Found |
|---|---|---|
| C | 62.59 | 62.33 |
| H | 9.10 | 9.16 |
| N | 4.87 | 4.78 |

The product was identified as N-(2,6-dimethyl-1-cyclohexen-1-yl)-N-(isobutoxymethyl)-2-chloroacetamide.

EXAMPLE 2

Alpha-chloro-N-(2,6-dimethylcyclohexen-1-yl)-N-(methoxymethyl) acetamide (5.3 g, 0.022 mol) and one half ml of methane sulfonic acid were refluxed in 150 ml of isopropanol through a soxhlet extractor filled with 22 g of activated 3A molecular sieve in the thimble. Contents were refluxed for 3 hours. Solvent removed in vacuo and residue washed with 100 ml of 5% Na$_2$CO$_3$ aqueous, then extracted with ether which was dried over MgSO$_4$, filtered and evaporated to give an oil which was put through silica gel with 3:2 hexane/ether. Fractions containing pure product (monitored by GLC) were combined and evaporated to give 3.3 g of an oil which was Kugelrohred (115° C. at 0.05 mm) obtaining 3.0 g (50%) of clear colorless oil.

Anal. for C$_{14}$H$_{24}$ClNO$_2$(%):

| Element | Calc'd | Found |
|---|---|---|
| C | 61.41 | 61.24 |
| H | 8.84 | 8.86 |
| N | 5.12 | 5.10 |

The product was identified as N-(2,6-dimethyl-1-cyclohexen-1-yl)-N-(isopropoxymethyl)-2-chloroacetamide.

EXAMPLE 3

Alpha-chloro-N-(2,6-dimethyl-1-cyclohexen-1-yl)-N-(methoxymethyl) acetamide (5.4 g, 0.022 mol), propargyl alcohol (12 g, 0.22 mol), five drops of methane sulfonic acid and 200 ml of benzene were refluxed through a soxhlet extractor filled with 22 g of activated 3A molecular sieves in a thimble. Refluxed at 80° C. for one hour. Washed with 100 ml of 5% Na$_2$CO$_3$ aqueous. Benzene layer extracted and solvent removed in vacuo leaving 5.5 g of an amber oil which was put through 75 g of silica gel with 3:2 hexane/ether. Fractions containing product (monitored by GLC) were evaporated giving 3.9 g which was Kugelrohred (150° C. at 0.1 mm) to obtain 3.1 g of clear colorless oil; 52% yield.

Anal. for C$_{14}$H$_{20}$ClNO$_2$(%):

| Element | Calc'd | Found |
|---|---|---|
| C | 62.33 | 62.15 |
| H | 7.47 | 7.48 |
| N | 5.19 | 5.15 |

The product was identified as N-(2,6-dimethyl-1-cyclohexen-1-yl)-N-(propargyloxymethyl)-2-chloroacetamide.

EXAMPLE 4

α-Chloro-N-(methoxymethyl)-N-(2,6-dimethyl-1-cyclohexen-1-yl) acetamide (5.1 g, 0.02 mol), 200 ml t-butanol and six drops of methane sulfonic acid were refluxed with a soxhlet extractor containing a thimble of 22 g of activated 3A molecular sieve. Refluxed 24 hours. Volatiles removed in vacuo. Residue taken up in methylene chloride and washed with water, dried over MgSO$_4$, filtered, and solvent removed in vacuo leaving 4.1 g oil. Oil was column chromatographed through silica gel using 3:2 hexane/ether as eluant. Fr. 2 and 3 held pure product as assayed by GLC. Evaporation of solvent left 3.2 g oil which was Kugelrohred (120° C. at 0.05 mm) to give 2.5 g of clear colorless oil; 53% yield.

Anal. for C$_{15}$H$_{26}$ClNO$_2$(%):

| Element | Calc'd | Found |
|---|---|---|
| C | 62.59 | 62.38 |
| H | 9.10 | 9.10 |
| N | 4.87 | 4.83 |

The product was identified as N-(2,6-dimethyl-1-cyclohexen-1-yl)-N-(t-butoxymethyl)-2-chloroacetamide.

EXAMPLE 5

2',6'-Diethyl-N-(methoxymethyl)-2-chloroacetanilide (5 g, 0.019 mol), ethyl glycolate (6.2 g, 0.06 mol), five drops of methane sulfonic acid and 150 ml benzene were refluxed in a soxhlet extractor with a thimble containing 22 g of activated 3A molecular sieve. Refluxed 11 hours. Contents washed with 150 ml water. Benzene layer extracted and solvent removed in vacuo leaving oil which was column chromatographed through silica gel with 3:2 hexane/ether as elutant. Fractions holding pure product (assayed by GLC) were evaporated to give 2.0 g oil which was Kugelrohred, bp 172° C. (0.05 mm), to give 1.7 g of clear colorless oil.

Anal. for C$_{17}$H$_{24}$ClNO$_4$(%):

| | Calc'd | Found |
|---|---|---|
| C | 59.73 | 59.52 |
| H | 7.08 | 7.11 |
| N | 4.10 | 4.07 |

The product was identified as 2',6'-diethyl-N-(1-carboethoxymethoxymethyl-2-chloaoracetanilide.

EXAMPLE 6

N,6'-[bis-(methoxymethyl)]-α-chloro-o-acetotoluidide, 3.0 g was dissolved in ca 75 ml ethanol with 5 microdrops of $CH_3SO_3H$ and refluxed under a soxhlet extractor filled with 3A molecular sieve. Overnight heating was necessary to drive the reaction to completion. The material vacuum treated, taken up in benzene, washed with benzene, then eluted through a silica gel column (3:2 hexane:ether) to give 2.1 g yield of oil as product; 70% yield.

Anal. for $C_{14}H_{20}ClNO_3$(%):

| C | Calc'd | Found |
|---|---|---|
| C | 58.84 | 59.86 |
| H | 7.05 | 7.14 |
| N | 4.90 | 4.94 |

The product was identified as 2'-methyl-6'-(methoxymethyl)-N-(ethoxymethyl)-2-chloroacetanilide.

EXAMPLE 7

Alpha-chloro-N-(2,6-dimethyl-1-cyclohexen-1-yl)-N-(methoxymethyl) acetamide (5 g, 0.02 mol), acetone cyanohydrin (10 g, 0.12 mol), ten drops of methane sulfonic acid and 100 ml xylene were refluxed with a soxhlet extractor containing 22 g of activated 3A molecular sieve in the thimble. Refluxed 2 hours. Allowed to cool, washed with 5% $Na_2CO_3$, and stripped in vacuo leaving 6.8 g of light amber oil. The oil was column chromatographed through 200 g of silica gel with 3:2 hexane/ether as eluant. Evaporation of fractions 4–6 held 4.5 g of light yellow oil which was Kugelrohred, bp 140° C. at 0.05 mm to give 2.9 g (49% yield) of light yellow oil.

Anal. for $C_{15}H_{23}ClN_2O_2$:

| Element | Calc'd | Found |
|---|---|---|
| C | 60.29 | 60.29 |
| H | 7.76 | 7.76 |
| N | 9.38 | 9.37 |

The product was identified as N-(2,6-dimethyl-1-cyclohexen-1-yl)-N-(1,1-dimethyl-1-cyanomethoxymethyl)-2-chloroacetamide.

EXAMPLE 8

Five milliliters of 10% boron trifluoride in methanol was added to a flask containing 0.2 g (0.7 mmol) of 2',6'-dimethyl-N-isobutoxymethyl-2-chloroacetanilide and the mixture allowed to stand at 10° C. for 6 hours. Methanol was then removed, water added and the product taken up in ether and washed with water. Thorough drying in $MgSO_4$ followed by removal of solvent and filtration of the product through a Florisil column gave 125.3 mg of clear oil from which was crystallized a cream colored solid, mp 37°–38° C.

Anal. for $C_{12}H_{16}ClNO_2$(%):

| Element | Calc'd | Found |
|---|---|---|
| C | 59.6 | 59.7 |
| H | 6.7 | 6.8 |
| Cl | 14.7 | 14.9 |

The product was identified by NMR and IR spectra as 2',6'-dimethyl-N-(methoxymethyl)-2-chloroacetanilide.

EXAMPLE 9

Following the procedure described in the preceding example, but substituting isopropanol for methanol and heating the reaction mixture to 45° C., 2',6'-dimethyl-N-(isopropoxymethyl)-2-chloroacetanilide was prepared; the product was a colorless oil, bp 130°–132° C. (0.4 mm Hg).

Anal. for $C_{14}H_{20}ClNO_2$(%):

| Element | Calc'd | Found |
|---|---|---|
| C | 62.3 | 62.2 |
| H | 7.6 | 7.6 |
| Cl | 13.1 | 13.3 |

Ten milliliters of n-butanol containing one milliliter of boron trifluoride etherate ($BF_3 \cdot (C_2H_5)_2O$) were added to a reactor containing 2.0 g of 2',6'-diethyl-N-(methoxymethyl)-2-chloroacetanilide; the mixture was allowed to equilibrate at room temperature for 2.0 hours, then heated to 80°–85° C. for 3.0 hours under a calcium chloride tube. The reaction mixture was poured over ice, neutralized with sodium bicarbonate, then extracted with ether and dried over sodium sulfate and concentrated to obtain 2.04 gm of product, a sample of which was analyzed by gas chromatography. The desired product, 2',6'-diethyl-N-(n-butoxymethyl)-2-chloroacetanilide, was obtained in 83% yield, bp 165° C. at 0.5 mm Hg.

Anal. for $C_{17}H_{26}ClNO_2$(%):

| Element | Calc'd | Found |
|---|---|---|
| C | 65.5 | 65.6 |
| H | 8.4 | 8.6 |
| N | 11.4 | 11.4 |

EXAMPLE 11

This example describes the preparation of 2'-methoxy-6'-methyl-N-(isopropoxymethyl)-2-chloroacetanilide.

2'-methoxy-6'-methyl-N-(methoxymethyl)-2-chloroacetanilide (0.025 mol) in 100–150 ml of isopropanol containing about 0.02 mol of methane sulphonic acid was refluxed under a Soxhlet extraction apparatus the thimble of which contained activated 3A Molecular Sieves (25 g) to absorb the liberated methanol. The course of the reaction was followed by glc. When reaction was complete, the excess alcohol was removed in vacuo and the residue taken up in ether or chloroform. The solution was washed with 5% sodium carbonate solution, dried ($Mg_2SO_4$) and evaporated. The product was purified by Kugelrohr distillation. Yield, 55%; pale amber solid, mp 40°–51° C.

Anal. for $C_{14}H_{20}ClNO_3$(%):

| Element | Calc'd | Found |
|---|---|---|
| C | 58.84 | 58.55 |
| H | 7.05 | 7.08 |
| N | 4.90 | 4.89 |
| Cl | 12.41 | 12.45 |

The product was identified as described in the lead sentence of this example.

EXAMPLES 12–77

Following the same general procedures described in Examples 1–11, but substituting the appropriate starting materials and reaction conditions, other 2-haloacetamides according to Formula I above are prepared by transetherification of N-methylene ether-2-haloacetamides with the appropriate alcohol to yield the corresponding N-methylene ether-2-haloacetamide. The same or equivalent solvents, acid catalysts and molecular sieves, together with appropriate temperatures and times are readily used in these process embodiments. Typical other compounds prepared in accordance with the above procedures are shown in Table I together with certain of their physical properties.

TABLE I

| Example No. | Compound | Empirical Formula | B.P. °C. (mm Hg) | Element | Analysis Calc'd | Found |
|---|---|---|---|---|---|---|
| 12 | N-(2,6-dimethyl-1-cyclohexen-1-yl)-N-(n-butoxymethyl)-2-chloroacetamide | $C_{15}H_{26}ClNO_2$ | 132(0.05) | C<br>Cl<br>N | 62.59<br>12.33<br>4.87 | 62.39<br>12.16<br>4.95 |
| 13 | N-(2,6-dimethyl-1-cyclohexen-1-yl)-N-(n-propoxymethyl)-2-chloroacetamide | $C_{14}H_{24}ClNO_2$ | 115(0.05) | C<br>H<br>N | 61.41<br>8.84<br>5.12 | 61.51<br>8.84<br>5.18 |
| 14 | N-(2,6-dimethyl-1-cyclohexen-1-yl)-N-(sec-butoxymethyl)-2-chloroacetamide | $C_{15}H_{26}ClNO_2$ | 133(0.05) | C<br>H<br>N | 62.59<br>9.10<br>4.87 | 62.44<br>9.13<br>4.82 |
| 15 | N-(2,6-dimethyl-1-cyclohexen-1-yl)-N-(2-chloroethoxymethyl)-2-chloroacetamide | $C_{13}H_{21}Cl_2NO_2$ | 150(0.05) | C<br>H<br>N | 53.07<br>7.19<br>4.76 | 52.94<br>7.25<br>4.68 |
| 16 | N-(2,6-dimethyl-1-cyclohexen-1-yl)-N-(2-butenoxymethyl)-2-chloroacetamide | $C_{15}H_{24}ClNO_2$ | 140(0.05) | C<br>H<br>N | 63.04<br>8.46<br>4.90 | 62.86<br>8.54<br>4.81 |
| 17 | N[2-(1-methylpropyl)-1-cyclohexen-1-yl]-N-(n-propoxymethyl)-2-chloroacetamide | $C_{16}H_{28}ClNO_2$ | 146(0.05) | C<br>H<br>N | 63.66<br>9.35<br>4.64 | 63.75<br>9.42<br>4.66 |
| 18 | N-(2-ethyl-1-cyclohexen-1-yl)-N-(allyloxymethyl)-2-chloroacetamide | $C_{14}H_{22}ClNO_2$ | 124(0.05) | C<br>H<br>N | 61.87<br>8.16<br>5.15 | 61.68<br>8.17<br>5.14 |
| 19 | N-(2,6-dimethyl-1-cyclohexen-1-yl)-N-(2-ethoxyethoxymethyl)-2-chloroacetamide | $C_{15}H_{26}ClNO_3$ | — | C<br>H<br>N | 59.30<br>8.63<br>4.61 | 59.20<br>8.63<br>4.61 |
| 20 | N-(1-methyl-1-cyclohexen-1-yl)-N-(n-butoxymethyl)-2-chloroacetamide | $C_{14}H_{24}ClNO_2$ | 132(0.05) | C<br>H<br>N | 61.41<br>8.84<br>5.12 | 61.32<br>9.12<br>4.85 |
| 21 | N-(2,6-dimethyl-1-cyclohexen-1-yl)-N-(2-methoxyethoxymethyl)-2-chloroacetamide | $C_{14}H_{24}ClNO_3$ | 140(0.05) | C<br>H<br>N | 58.02<br>8.35<br>4.83 | 57.84<br>8.41<br>4.80 |
| 22 | N-(2,6-dimethyl-1-cyclohexen-1-yl)-N-(3,3-dichloro-2-propenoxymethyl)-2-chloroacetamide | $C_{14}H_{20}Cl_3NO_2$ | 173(0.25) | C<br>H<br>N | 49.36<br>5.92<br>4.11 | 49.17<br>5.95<br>4.09 |
| 23 | N-(2,6-dimethyl-1-cyclohexen-1-yl)-N-(3-chloro-2-propenoxymethyl)-2-chloroacetamide | $C_{14}H_{24}Cl_2NO_2$ | 159(0.05) | C<br>H<br>N | 54.91<br>6.10<br>4.57 | 54.91<br>6.10<br>4.56 |
| 24 | N-(2,6-dimethyl-1-cyclohexen-1-yl)-N-(2,3,3-trichloro-2-propenoxymethyl)-2-chloroacetamide | $C_{14}H_{19}Cl_4NO_2$ | 173(0.1) | C<br>H<br>N | 44.83<br>5.11<br>3.73 | 44.78<br>5.14<br>3.71 |
| 25 | N-(2,6-dimethyl-1-cyclohexen-1-yl)-N-(2,3-dichloro-2-propenoxymethyl)-2-chloroacetamide | $C_{14}H_{20}Cl_3NO_2$ | 166(0.05) | C<br>H<br>N | 49.36<br>5.92<br>4.11 | 49.69<br>6.28<br>4.13 |
| 26 | N-(2,6-dimethyl-1-cyclohexen-1-yl)-N-(2-chloro-2-propenoxymethyl)-2-chloroacetamide | $C_{14}H_{21}Cl_2NO_2$ | 159(0.025) | C<br>H<br>N | 54.91<br>7.08<br>4.57 | 54.86<br>7.11<br>4.56 |
| 27 | N-(2,6-dimethyl-1-cyclohexen-1-yl)-N-(methallyloxymethyl)-2-chloroacetamide | $C_{15}H_{24}ClNO_2$ |  | C<br>H<br>N | 63.04<br>8.46<br>4.90 | 62.89<br>8.45<br>4.83 |
| 28 | N-(2,6-dimethyl-1-cyclohexen-1-yl)-N-(cyclopropoxymethyl)-2-chloroacetamide | $C_{15}H_{24}ClNO_2$ | 130(0.05) | C<br>H<br>N | 63.04<br>8.46<br>4.90 | 63.02<br>8.50<br>4.91 |
| 29 | N-(2,6-diethyl-1-cyclohexen-1-yl)-N-(n-propoxymethyl)-2-chloroacetamide | $C_{16}H_{28}ClNO_2$ | 140(0.05) | C<br>H<br>N | 63.66<br>9.35<br>4.64 | 63.61<br>9.35<br>4.62 |
| 30 | N-(2,6-diethyl-1-cyclohexen-1-yl)-N-(sec-butoxymethyl)-2-chloroacetamide | $C_{17}H_{38}ClNO_2$ | 137(0.05) | C<br>H<br>N | 64.64<br>9.57<br>4.43 | 64.50<br>9.63<br>4.39 |
| 31 | N-(2,6-diethyl-1-cyclohexen-1-yl)-N-(isopropoxymethyl)-2-chloroacetamide | $C_{16}H_{28}ClNO_2$ | 134(0.05) | C<br>H<br>N | 63.66<br>9.35<br>4.64 | 63.50<br>9.36<br>4.65 |
| 32 | N-(2,6-diethyl-1-cyclohexen-1-yl)-N-(n-butoxymethyl)-2-chloroacetamide | $C_{17}H_{30}ClNO_2$ | 155(0.05) | C<br>H<br>N | 64.64<br>9.57<br>4.43 | 64.58<br>9.59<br>4.44 |
| 33 | N-(2,6-diethyl-1-cyclohexen-1-yl)-N-(t-butoxymethyl)-2-chloroacetamide | $C_{17}H_{30}ClNO_2$ | 142(0.05) | C<br>H<br>N | 64.64<br>9.57<br>4.43 | 64.61<br>9.58<br>4.43 |
| 34 | N-(2,6-diethyl-1-cyclohexen-1-yl)-N-(1-methyl-propoxymethyl)-2-chloroacetamide | $C_{17}H_{30}ClNO_2$ | 156(0.05) | C<br>H<br>N | 64.64<br>9.57<br>4.43 | 64.53<br>9.60<br>4.43 |

TABLE I-continued

| Example No. | Compound | Empirical Formula | B.P.°C. (mm Hg) | Analysis Element | Calc'd | Found |
|---|---|---|---|---|---|---|
| 35 | N-(2,6-diethyl-1-cyclohexen-1-yl)-N-(allyloxymethyl)-2-chloroacetamide | $C_{16}H_{26}ClNO_2$ | 133(0.05) | C | 64.09 | 63.91 |
| | | | | H | 8.74 | 8.74 |
| | | | | N | 4.67 | 4.64 |
| 36 | N-(2,6-diethyl-1-cyclohexen-1-yl)-N-(2-propynyloxymethyl)-2-chloroacetamide | $C_{16}H_{24}ClNO_2$ | 146(0.05) | C | 64.53 | 64.48 |
| | | | | H | 8.12 | 8.12 |
| | | | | N | 4.70 | 4.70 |
| 37 | N-(2,6-diethyl-1-cyclohexen-1-yl)-N-(2-methoxyethoxymethyl)-2-chloroacetamide | $C_{16}H_{28}ClNO_3$ | 160(0.05) | C | 60.46 | 60.28 |
| | | | | H | 8.88 | 8.87 |
| | | | | N | 4.41 | 4.39 |
| 38 | N-(2,6-diethyl-1-cyclohexen-1-yl)-N-(2-methallyloxymethyl)-2-chloroacetamide | $C_{17}H_{28}ClNO_2$ | 140(0.05) | C | 65.06 | 64.93 |
| | | | | H | 8.99 | 9.00 |
| | | | | N | 8.46 | 8.43 |
| 39 | N-(2-methyl-1-cyclohexen-1-yl)-N-(1-methylpropoxymethyl)-2-chloroacetamide | $C_{14}H_{24}ClNO_2$ | 116(0.05) | C | 61.41 | 61.38 |
| | | | | H | 8.84 | 8.85 |
| | | | | N | 5.12 | 5.09 |
| 40 | N-(2-methyl-1-cyclohexen-1-yl)-N-(n-propoxymethyl)-2-chloroacetamide | $C_{13}H_{22}ClNO_2$ | 119(0.05) | C | 60.11 | 60.23 |
| | | | | H | 8.54 | 8.62 |
| | | | | N | 5.39 | 5.37 |
| 41 | N-(2-methyl-1-cyclohexen-1-yl)-N-(iso-propoxymethyl)-2-chloroacetamide | $C_{13}H_{22}ClNO_2$ | 107(0.05) | C | 60.11 | 60.02 |
| | | | | H | 8.54 | 8.58 |
| | | | | N | 5.39 | 5.35 |
| 42 | N-(2-isopropyl-1-cyclohexen-1-yl)-N-(allyloxymethyl)-2-chloroacetamide | $C_{15}H_{24}ClNO_2$ | 130(0.05) | C | 63.04 | 63.11 |
| | | | | H | 8.46 | 8.50 |
| | | | | N | 4.90 | 4.89 |
| 43 | N-(2-methyl-6-ethyl-1-cyclohexen-1-yl)-N-(allyloxymethyl)-2-chloroacetamide | $C_{15}H_{24}ClNO_2$ | 130(0.05) | C | 63.04 | 62.90 |
| | | | | H | 8.46 | 8.45 |
| | | | | N | 4.90 | 4.82 |
| 44 | N-(2-methyl-1-cyclohexen-1-yl)-N-(allyloxymethyl)-2-chloroacetamide | $C_{13}H_{20}ClNO_2$ | 124(0.05) | C | 60.58 | 60.54 |
| | | | | H | 7.82 | 7.83 |
| | | | | N | 5.43 | 5.41 |
| 45 | 2'-methyl-6'-ethyl-N-(ethoxymethyl)-2-chloroacetanilide | $C_{14}H_{20}ClNO_2$ | 125–130(0.3) | C | 62.3 | 62.4 |
| | | | | H | 7.9 | 7.6 |
| | | | | N | 13.1 | 13.3 |
| 46 | 2',6'-diethyl-N-(2,2-dimethyl-1,3-dioxolan-4-yl-methoxymethyl)-2-chloroacetanilide | $C_{19}H_{28}ClNO_4$ | 171(0.05) | C | 61.70 | 61.58 |
| | | | | H | 7.63 | 7.66 |
| | | | | N | 3.79 | 3.81 |
| 47 | 2',6'-diethyl-N-(3,3-dichloroallyloxymethyl)-2-chloroacetanilide | $C_{16}H_{20}Cl_3NO_2$ | 183(0.05) | C | 52.69 | 52.59 |
| | | | | H | 5.53 | 5.54 |
| | | | | N | 3.84 | 3.82 |
| 48 | 2',6'-diethyl-N-(3-chloroallyloxymethyl)-2-chloroacetanilide | $C_{16}H_{21}Cl_2NO_2$ | 166(0.05) | C | 58.19 | 58.10 |
| | | | | H | 6.41 | 6.42 |
| | | | | N | 4.24 | 4.25 |
| 49 | 2',6'-diethyl-N-(2,3,3-trichloroallyloxymethyl)-2-chloroacetanilide | $C_{16}H_{19}Cl_4NO_2$ | 173(0.05) | C | 48.15 | 48.28 |
| | | | | H | 4.80 | 4.86 |
| | | | | N | 3.51 | 3.49 |
| 50 | 2',6'-diethyl-N-(2,3-dichloroallyloxymethyl)-2-chloroacetanilide | $C_{16}H_{20}ClNO_2$ | 180(0.025) | C | 52.69 | 52.64 |
| | | | | H | 5.53 | 5.55 |
| | | | | N | 3.84 | 3.83 |
| 51 | 2',6'-dimethoxy-N-(n-propoxymethyl)-2-chloroacetanilide | $C_{14}H_{20}ClNO_4$ | M.P. 83–85° C. | C | 55.72 | 55.65 |
| | | | | H | 6.68 | 6.70 |
| | | | | N | 4.64 | 4.62 |
| 52 | 2',6'-dimethoxy-N-(n-butoxymethyl)-2-chloroacetanilide | $C_{15}H_{22}ClNO_4$ | 170(0.05) | C | 57.05 | 57.03 |
| | | | | H | 7.02 | 7.02 |
| | | | | N | 4.44 | 4.47 |
| 53 | 2',6'-diethyl-N-[(1,3-dioxolan-4-yl)methoxymethyl]-2-chloroacetanilide | $C_{17}H_{24}ClNO_4$ | 160(0.05) | C | 59.73 | 59.73 |
| | | | | H | 7.08 | 7.11 |
| | | | | N | 4.10 | 4.12 |
| 54 | 2',6'-diethyl-N-(ethoxymethyl)-2-chloroacetanilide | $C_{17}H_{23}ClN_2O_2$ | M.P. 48–54° C. | C | 63.25 | 63.15 |
| | | | | H | 7.18 | 7.21 |
| | | | | N | 8.68 | 8.65 |
| 55 | 2',6'-dimethyl-N-(allyloxymethyl)-2-bromoacetanilide | $C_{14}H_{18}BrNO_2$ | 157(0.05) | C | — | — |
| | | | | H | — | — |
| | | | | N | — | — |
| 56 | 2'-methyl-6'-(methoxymethyl)-N-(isopropoxymethyl)-2-chloroacetanilide | $C_{15}H_{22}ClNO_3$ | 136–138(0.1) | C | 60.10 | 60.32 |
| | | | | H | 7.40 | 7.03 |
| | | | | N | 4.67 | 4.65 |
| 57 | 2'-methoxy-6'-methyl-N-(ethoxymethyl)-2-chloroacetanilide | $C_{13}H_{18}ClNO_3$ | M.P. 170° C. | C | 57.46 | 57.19 |
| | | | | H | 6.67 | 6.70 |
| | | | | N | 5.16 | 5.11 |
| | | | | Cl | 13.05 | 13.09 |
| 58 | 2'-methoxy-6'-methyl-N-(1-methylpropoxymethyl)-2-chloroacetanilide | $C_{15}H_{22}ClNO_3$ | oil | C | 60.10 | 59.90 |
| | | | | H | 7.40 | 7.36 |
| | | | | N | 4.67 | 4.62 |
| | | | | Cl | 11.83 | 11.97 |
| 59 | 2'-ethoxy-6'-methyl-N-(allyloxymethyl)-2-chloroacetanilide | $C_{10}H_{20}ClNO_3$ | 110(0.07) | C | 60.50 | 60.30 |
| | | | | H | 6.77 | 6.80 |
| | | | | N | 4.70 | 4.64 |
| | | | | Cl | 11.91 | 11.69 |
| 60 | 2'-ethoxy-6'-methyl-N-(propargyloxymethyl)-2-chloroacetanilide | $C_{15}H_{18}ClNO_3$ | 140(0.1) | C | 60.91 | 60.98 |
| | | | | H | 6.13 | 6.14 |

TABLE I-continued

| Example No. | Compound | Empirical Formula | B.P.°C. (mm Hg) | Analysis Element | Calc'd | Found |
|---|---|---|---|---|---|---|
| | | | | N | 4.74 | 4.74 |
| | | | | Cl | 11.99 | 11.94 |
| 61 | 2'-ethoxy-6'-methyl-N-(1-methylpropoxymethyl)-2-chloroacetanilide | $C_{16}H_{24}ClNO_3$ | 135(0.09) | C | 61.24 | 60.98 |
| | | | | H | 7.71 | 7.69 |
| | | | | N | 4.46 | 4.42 |
| | | | | Cl | 11.30 | 11.22 |
| 62 | 2'-(trifluoromethyl)-6'-methyl-N-(ethoxymethyl)-2-chloroacetanilide | $C_{13}H_{15}ClF_3NO_2$ | 100–110(0.1) | C | 50.41 | 50.02 |
| | | | | H | 4.88 | 4.81 |
| | | | | N | 4.52 | 4.38 |
| 63 | 2'-(trifluoromethyl)-6'-ethyl-N-(ethoxymethyl)-2-chloroacetanilide | $C_{14}H_{17}ClF_3NO_2$ | 133–135(0.02) | C | 51.94 | 51.32 |
| | | | | H | 5.29 | 5.26 |
| | | | | N | 4.33 | 4.39 |
| 64 | 2'-(trifluoromethyl)-N-(ethoxymethyl-2-chloroacetanilide | $C_{12}H_{13}ClF_3NO_2$ | m.p. 48–51 | C | 48.83 | 48.74 |
| | | | | H | 4.43 | 4.43 |
| | | | | N | 4.75 | 4.74 |
| 65 | 2'-(trifluoromethyl)-6'-ethyl-N-(methoxymethyl)-2-chloroacetanilide | $C_{13}H_{15}ClF_3NO_2$ | 135(0.02) | C | 50.41 | 50.44 |
| | | | | H | 4.88 | 4.85 |
| | | | | N | 4.52 | 4.53 |
| 66 | 2'-(trifluoromethyl)-6'-ethyl-N-(n-butoxymethyl)-2-chloroacetanilide | $C_{16}H_{21}ClF_3NO_2$ | 155(0.02) | C | 54.63 | 54.42 |
| | | | | H | 6.02 | 6.03 |
| | | | | N | 3.98 | 3.97 |
| 67 | 2'-(trifluoromethyl)-N-(isobutoxymethyl)-2-chloroacetanilide | $C_{14}H_{17}ClF_3NO_2$ | 120–125(0.05) | C | 51.94 | 52.35 |
| | | | | H | 5.29 | 5.38 |
| | | | | N | 4.33 | 4.26 |
| 68 | 2'-(2-methoxyethoxy)-6'-methyl-N-(isopropoxymethyl)-2-chloroacetanilide | $C_{16}H_{24}ClNO_4$ | — | C | 58.27 | 58.09 |
| | | | | H | 7.33 | 7.34 |
| | | | | N | 4.25 | 4.26 |
| | | | | Cl | 10.75 | 10.79 |
| 69 | 2'-(2-methoxyethoxy)-6'-methyl-N-(2-propenyloxymethyl)-2-chloroacetanilide | $C_{16}H_{22}ClNO_4$ | 140(0.03) | C | 58.62 | 58.53 |
| | | | | H | 6.76 | 6.79 |
| | | | | N | 4.27 | 4.24 |
| | | | | Cl | 10.82 | 10.86 |
| 70 | 2'-tetrahydrofurfuryloxy-5'-trifluoromethyl-N-(2-propenyloxymethyl)-2-chloroacetanilide | $C_{12}H_{21}ClF_3NO_4$ | 140(0.07) | C | 53.01 | 53.09 |
| | | | | H | 5.19 | 5.23 |
| | | | | N | 3.43 | 3.40 |
| | | | | Cl | 8.69 | 8.74 |
| 71 | 2'-(2-methoxyethoxy)-N-(2-methoxyethoxymethyl)-2-chloroacetanilide | $C_{15}H_{22}ClNO_5$ | 155(0.09) | C | 54.30 | 54.26 |
| | | | | H | 6.68 | 6.69 |
| | | | | N | 4.22 | 4.23 |
| | | | | Cl | 10.69 | 10.68 |
| 72 | 2'-t-butyl-6'-chloro-N-(methoxymethyl)-2-chloroacetanilide | $C_{14}H_{19}Cl_2NO_2$ | 146(0.0) | C | 55.27 | 55.24 |
| | | | | H | 6.30 | 6.32 |
| | | | | N | 4.60 | 4.66 |
| 73 | 2'-nitro-(N-isobutoxymethyl)-2-chloroacetanilide | $C_{13}H_{17}ClN_2O_4$ | 155–165(0.4) | C | 51.92 | 52.62 |
| | | | | H | 5.70 | 5.83 |
| | | | | N | 9.31 | 9.21 |
| 74 | 2'-t-butyl-6'-chloro-N-(methoxymethyl)-2-chloroacetanilide | $C_{16}H_{23}Cl_2NO_2$ | mp 83–86° C. | C | 57.84 | 57.92 |
| | | | | H | 6.98 | 7.03 |
| | | | | N | 4.22 | 4.24 |
| 75 | 2'-isobutoxy-6'-methyl-N-(n-propoxymethyl)-2-chloroacetanilide | $C_{17}H_{26}ClNO_3$ | 130(0.04) | C | 62.28 | 62.27 |
| | | | | H | 7.99 | 8.01 |
| | | | | Cl | 10.81 | 10.81 |
| 76 | 2'-isobutoxy-6'-ethyl-N-(ethoxymethyl)-2-chloroacetanilide | $C_{17}H_{26}ClNO_3$ | 132(0.07) | C | 62.28 | 62.27 |
| | | | | H | 7.99 | 8.02 |
| | | | | Cl | 10.81 | 10.82 |
| 77 | 2'-n-butoxy-6'-ethyl-N-(2-propenyloxymethyl)-2-chloroacetanilide | $C_{18}H_{26}ClNO_3$ | 123(0.04) | C | 63.61 | 63.60 |
| | | | | H | 7.71 | 7.74 |
| | | | | Cl | 10.43 | 10.42 |
| 78 | 2'-t-butyl-6'-chloro-N-(ethoxymethyl)-2-bromoacetanilide | $C_{15}H_{21}BrClNO_2$ | mp 71–76° C. | C | 49.67 | 49.25 |
| | | | | H | 5.84 | 5.82 |
| | | | | N | 3.86 | 3.87 |
| 79 | 2'-t-butyl-6'-chloro-N-(2-propen-1-yloxymethyl)-2-chloroacetanilide | $C_{16}H_{21}Cl_2NO_2$ | mp 42–47° C. | C | 58.19 | 58.02 |
| | | | | H | 6.41 | 6.50 |
| | | | | N | 4.24 | 4.18 |

The process of this invention is of wide applicability as indicated in the above working embodiments. Still further, the process of this invention may be suitably used to prepare a variety of other 2-haloacetamides from the appropriate N-alkoxymethyl or other N-methylene ether starting material. Since the reactive site in the transetherification process is at the N-methylene ether position, a wide variety of substituents may occupy the other non-haloacetyl position in the amide. That is, in Formula II herein, in addition to the R members exemplified above, other R members are within the purview of this invention. Thus, R may be hydrogen, aliphatic, cycloaliphatic, heterocyclic or aromatic members, including alkyl, alkenyl, alkynyl, cycloalkyl, alkylcycloalkyl, N-, O-, or S-heterocyclic radicals, which members may be independently substituted with non-interfering radicals, e.g., alkyl, halogen, nitro, amino, $CF_3$, hydroxyl, alkoxy, polyalkoxy, alkoxyalkyl and the like.

Suitable solvents which may be used herein include the R'OH alcohols defined in Formula III above, aliphatic and aromatic hydrocarbons or halogenated hydrocarbons such as naphtha, the halogenated alkanes, e.g., $CCl_4$, $CHCl_3$, ethylene dichloride, trichloroethane, etc., benzene, halogenated benzenes, toluene, the xylenes and other inert solvents.

Other acid catalysts which may be used in the process of this invention include inorganic acids such as $H_2SO_4$, $H_3PO_4$; the hydrohalides, HCl, HBr, HI; sulfonic acids such as sulphamic acid, benzenesulfonic acid, p-toluenesulfonic acid, etc.; Lewis Acids, e.g., $BF_3$, $BF_3$ etherates, $AlCl_3$, etc. It is within the purview of this invention to use salts of organic acids as acidic catalysts. Examples of such salts are the halides and acetates, oxalates, etc., of boron, copper and mercury. It is also within the purview of this invention to use acidic ion-exchange resins such as sulphonated styrene polymers or co-polymers which may contain from 1–15% by weight of a cross-linking agent such as divinylbenzene.

Molecular sieves which may be used herein include natural zeolites (alumino-silicates) or synthetic zeolites such as alkali metal alumino-silicate hydrates exemplified by Type 3A, i.e., $K_9Na_3[(AlO_2)_{12}(SiO_2)_{12}]\cdot 27H_2O$; Type 4A, i.e., $Na_{12}[(AlO_2)_{12}(SiO_2)_{12}]\cdot 27H_2O$; Type 5A, i.e., $Ca_{4-5}Na_3[(AlO_2)_{12}]\cdot 3H_2O$, etc. The criteria for selection of a particular molecular sieve is that its intercellular pore size be small enough to trap or absorb by-product alcohol while excluding larger molecules. As used herein molecular sieves are preferably used to absorb methanol and water in embodiments in which these by-products are formed.

As noted above, the compounds of this invention have been found to be effective as herbicides. While most of the compounds described herein are known, some are novel and are the inventions of other inventive entities employed by the assignee herein; the present invention does not claim any novel compounds.

It will be appreciated by those skilled in the art that the process of this invention may be modified in non-inventive modes by those skilled in the art having particular reference to the nature and ratio of reactants, particular species within the defined genus of reactants, catalysts, solvents, reaction temperatures, times, pressures, etc.

We claim:

1. Process for the preparation of N-methylene ether-substituted 2-haloacetamides having the formula

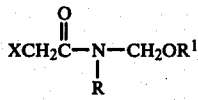    I which comprises transetherification of N-methylene ether-2-haloacetamides of the formula

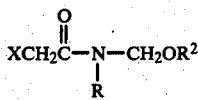    II with a compound of the formula

    III wherein the above formulae
X is chloro, bromo or iodo,
R is a phenyl or cycloalkenyl radical or a phenyl or cycloalkenyl radical substituted with lower alkyl, alkoxy, polyalkoxy or alkoxymethyl having up to 6 carbon atoms, halogen, $NO_2$, $-CF_3$ or a tetrahydrofurfuryloxy radical containing up to 6 carbon atoms, and
$R^1$ and $R^2$ are different $C_{1-6}$ alkyl, haloalkyl, alkenyl, haloalkenyl, alkynyl, haloalkynyl, alkoxyalkyl, cycloalkyl, cyanoalkyl or lower alkoxycarboalkyl radicals or 1,3-dioxolanylmethyl which may be substituted with lower alkyl groups, said transetherification being conducted in an inert solvent at elevated temperature and in the presence of an acid catalyst.

2. Process according to claim 1 wherein $R^1$ and $R^2$ are both different $C_{1-6}$ alkyl radicals.

3. Process according to claim 2 wherein R is a phenyl radical substituted in at least one ortho position with a $C_{1-6}$ alkyl, alkoxy, polyalkoxy or alkoxymethyl radical having up to 6 carbon atoms, halogen, $NO_2$, $-CF_3$ or a tetrahydrofurfuryloxy radical containing up to 6 carbon atoms.

4. Process according to claim 3 wherein said phenyl radical is substituted in both ortho positions with $C_{1-6}$ alkyl radicals which may be the same or different.

5. Process according to claim 4 wherein said alkyl radicals are independently methyl, ethyl or isopropyl and $R_1$ and $R_2$ are different $C_{1-4}$ alkyl groups.

6. Process for preparing 2',6'-diethyl-N-(n-butoxymethyl)-2-chloroacetanilide which comprises reacting 2',6'-diethyl-N-(methoxymethyl)-2-chloroacetanilide with n-butanol in the presence of an acid catalyst.

7. Process for preparing 2',6'-diethyl-N-(methoxymethyl)-2-chloroacetanilide which comprises reacting 2',6'-diethyl-N-(n-butoxymethyl)-2-chloroacetanilide with methanol in the presence of an acid catalyst.

8. Process for preparing 2'-methyl-6'-ethyl-N-(ethoxymethyl)-2-chloroacetanilide which comprises reacting 2'-methyl-6'-ethyl-N-(methoxymethyl)-2-chloroacetanilide with ethanol in the presence of an acid catalyst.

9. Process according to claim 3 wherein R is a phenyl radical substituted with methyl, ethyl or isopropyl in one ortho position and a $C_{1-6}$ alkoxy radical in the other ortho position and $R^1$ and $R^2$ are different $C_{1-4}$ alkyl radicals.

10. Process for preparing 2'-methoxy-6'-methyl-N-(isopropoxymethyl)-2-chloroacetanilide which comprises reacting 2'-methoxy-6'-methyl-N-(methoxymethyl)-2-chloroacetanilide with isopropanol in the presence of an acid catalyst.

11. Process for preparing 2'-isobutoxy-6'-methyl-N-(n-propoxymethyl)-2-chloroacetanilide which comprises reacting 2'-isobutoxy-6'-methyl-N-(methoxymethyl)-2-chloroacetanilide with n-propanol in the presence of an acid catalyst.

12. Process for preparing 2'-isobutoxy-6'-ethyl-N-(ethoxymethyl)-2-chloroacetanilide which comprises reacting 2'-isobutoxy-6'-methyl-N-(methoxymethyl)-2-chloroacetanilide with ethanol in the presence of an acid catalyst.

13. Process according to claim 3 wherein R is a phenyl radical substituted with a $-CF_3$ radical in one ortho position and a methyl or ethyl radical in the other ortho position and $R^1$ and $R^2$ are different $C_{1-4}$ alkyl radicals.

14. Process for preparing 2'-trifluoromethyl-6'-methyl-N-(ethoxymethyl)-2-chloroacetanilide which comprises reacting 2'-trifluoromethyl-6'-methyl-N-(methoxymethyl)-2-chloroacetanilide with ethanol in the presence of an acid catalyst.

15. Process for preparing 2'-trifluoromethyl-6'-ethyl-N-(ethoxymethyl)-2-chloroacetanilide which comprises reacting 2'-trifluoromethyl-6'-ethyl-N-(methoxymethyl)-2-chloroacetanilide with ethanol in the presence of an acid catalyst.

16. Process according to claim 3 where R is a cycloalken-1-yl radical substitutes with $C_{1-6}$ alkyl radicals in both ortho positions.

17. Process for preparing N-(2,6-dimethyl-1-cyclohexen-1-yl)-N-(isobutoxymethyl)-2-chloroacetanilide which comprises reacting N-(2,6-dimethyl-1-cyclohexen-1-yl)-N-(methoxymethyl)-2-chloroacetanilide with isobutanol in the presence of an acid catalyst.

18. Process according to any of claims 1-14 or 15 which is conducted in the presence of a molecular sieve.

19. Process according to any of claims 1-15 or 16 wherein said acid catalyst is $BF_3.(C_2H_5)_2O$ or methane sulfonic acid.

* * * * *